(12) United States Patent
Gauger et al.

(10) Patent No.: US 6,321,764 B1
(45) Date of Patent: Nov. 27, 2001

(54) COLLAPSIBLE ISOLATION APPARATUS

(75) Inventors: James R. Gauger, Highland Park; Robert L. Mullins, Chicago, both of IL (US); George L. Stefanek, Beverly Shores, IN (US); Joseph J. Petrovic, Burr Ridge, IL (US)

(73) Assignee: IIT Research Institute, Chicago, IL (US)

( * ) Notice: Subject to any disclaimer, the term of this patent is extended or adjusted under 35 U.S.C. 154(b) by 0 days.

(21) Appl. No.: 09/379,962

(22) Filed: Aug. 24, 1999

Related U.S. Application Data (60) Provisional application No. 60/113,503, filed on Dec. 21, 1998.

(51) Int. Cl.[7] .................................................. E04H 15/36
(52) U.S. Cl. ...................................................... 135/128
(58) Field of Search ................................. 135/128, 116, 135/117; 128/202.16, 202.12

(56) References Cited

U.S. PATENT DOCUMENTS

| | | | |
|---|---|---|---|
| 2,683,262 | 7/1954 | Foss ............................... | 2/2 |
| 2,985,129 | 5/1961 | Kirkpatrick ..................... | 113/111 |
| 3,118,401 | 1/1964 | Platt ............................... | 109/1 |
| 3,119,358 | 1/1964 | Colson et al. ................... | 109/1 |
| 3,265,059 | * 8/1966 | Matthews ........................ | 135/117 |
| 3,272,199 | * 9/1966 | Matthews ........................ | 135/117 |
| 3,695,507 | 10/1972 | Sams ............................... | 229/53 |
| 3,766,844 | 10/1973 | Donnelly et al. ................ | 98/33 |
| 3,840,919 | * 10/1974 | Middleton ....................... | 135/117 |
| 4,000,749 | 1/1977 | Busco ............................. | 135/1 |
| 4,198,996 | * 4/1980 | Keable et al. ................... | 135/128 |
| 4,352,991 | 10/1982 | Kaufman ......................... | 307/9 |
| 4,389,066 | 6/1983 | Weir et al. ...................... | 296/19 |
| 4,584,989 | 4/1986 | Stith ............................... | 128/1 |
| 4,736,762 | 4/1988 | Wayman ......................... | 135/88 |
| 5,314,377 | 5/1994 | Pelosi, III ....................... | 454/187 |
| 5,331,991 | 7/1994 | Nilsson .......................... | 135/93 |
| 5,343,887 | * 9/1994 | Danaher ......................... | 135/128 |
| 5,626,151 | 5/1997 | Linden ........................... | 128/897 |
| 5,630,296 | 5/1997 | Kendall, Jr. .................... | 52/2.11 |
| 5,725,426 | 3/1998 | Alvarez .......................... | 454/187 |
| 5,881,405 | * 3/1999 | Garrigues ....................... | 135/117 |

* cited by examiner

*Primary Examiner*—Alvin Chin-Shue
*Assistant Examiner*—Sarah Purol
(74) *Attorney, Agent, or Firm*—Fitch, Even, Tabin & Flannery (57) ABSTRACT

A collapsible personnel isolation apparatus for preventing unwanted contaminations of hazardous biological and chemical materials including a base. A cover connects to the base by way of a zipper. A plurality of glove box ports are provided to allow rapid and convenient treatment of the patient.

21 Claims, 10 Drawing Sheets

COLLAPSIBLE ISOLATION APPARATUS

CROSS REFERENCE TO RELATED APPLICATION

Priority is claimed from U.S. provisional application Ser. No. 60/113,503, filed Dec. 21, 1998.

GOVERNMENTAL RIGHTS

The subject matter disclosed and claimed herein was developed under Department of Defense Contract No. DLA900-93-D-0011/0038. The government has certain rights in the invention.

BACKGROUND OF THE INVENTION

The invention relates to isolation pods and particularly to a collapsible low cost pod for isolating a person previously exposed to a chemical or biological hazard from a safe environment, or in the alternative, for isolating an unexposed person from a hazardous environment for medical transport.

The threat to health from biological and chemical contaminants has, if anything, increased over the last several years. The popular press is full of accounts of potential biological attacks which might either be privately or state sponsored. Chemical terrorist attacks have already occurred in various areas of the world and certain governments have engaged in chemical attacks against enemies and even members of their own society. While the risks from chemical attacks are believed to be substantial, in the future the threat of biological attack may continue to increase and may become more significant than chemical attacks.

Apparatus are currently available for transporting victims of natural biological hazards. Such victims may include persons who have been infected with Ebola or Marburg virus, anthrax or the like. One such system is the so-called Vickers box which comprises a relatively self-contained unit having an external frame with a biological hazard barrier comprising sheet polyvinyl chloride sheet suspended therefrom. The frame has a foot rest or step. A lower substantially oval loading port provides access to the interior through which a patient may be carried to rest on a stretcher-like structure. The barrier has a ventilation tube entering its foot end. Glove ports are formed on the sides of the frame thereof. A pass-through port extends through the barrier near where the calves of a patient would normally rest. There are pairs of glove ports on each side of the unit. Intravenous bags and the like may be suspended from the frame of the unit. An intravenous line may extend through a port in the side of the unit. The Vickers box weighs over 200 pounds unloaded. In addition, the Vickers box is not disposable and is very expensive. It typically costs $20,000 to $30,000. When assembled the Vickers frames are bulky and the unit is simply not adapted for storage in large numbers for use in the event of a biological emergency. In addition it cannot be transported in all types of military evac vehicles.

Another approach has been taken in U.S. Pat. No. 5,626,151 to Linden. Linden discloses a transportable life support system including a base 2, a stretcher 3, and a rigid cover 4. The base may be constructed from a fiber reinforced resin composite. Medical equipment is housed within the base including a ventilator 11, an oxygen source 12 such as an oxygen tank or oxygen generator, a suction unit 13 and an environmental control unit 14. A high volume intravenous pump 23, a pulse oximetry sensor 24 a blood pressure sensor 25 and electrocardiography sensor all are relatively bulky and may or may not be needed for the treatment for the particular patient depending upon whether the patient had merely been exposed or has been infected. The environmental control unit includes means for providing contaminant-free air to the unit including at least one filter 14B, which may be a typical nuclear-biological-chemical type filter. The problem with such a unit is that it appears to be relatively bulky because of the built-in components in the base of the unit and the unit may not quickly and easily be stored in a compact configuration and may represent overkill for a variety of hazards.

What is needed then is an inexpensive easily transportable compact biological isolation system for use in isolating victims in a chemical or bioterror event.

SUMMARY OF THE INVENTION

A collapsible personnel isolation apparatus for isolating an individual who may have been exposed or has been infected with a biological agent or may have been exposed with a chemical agent embodies the present invention and is particularly well adapted for compact storage. The collapsible personnel isolation system embodying the present invention may include a pod, a suit or a flexible wrap. The system is inexpensive, may be completely disposed by burning or the like, and provides facilities for a variety of medical interventions without the necessity that expensive treatment equipment be associated therewith.

The system includes a flexible base, which may be made from polyvinyl chloride material and which is tear resistant. Specifically the base includes an outer sheet and an inner sheet. Each of the inner and outer sheets has first and second polyvinyl chloride outer layers with an intermediate nylon mesh layer positioned between. A nylon webbing formed in the shape of a ladder includes a pair of upright or runner elements extending longitudinally on opposite sides of the base for providing support when the base is carried. The nylon webbing is positioned between the inner and outer sheets. This prevents the base from tearing and provides support to handholds in the base. Lateral or central spine type support is provided by five nylon web strips connecting the two longitudinal strips.

Rectangular handholds are formed adjacent to the elongated nylon uprights for grasping by persons carrying the patient. If the patient is being carried by stretcher, grommets formed in the walls of the sheets accept hooks, cords or other tension members. The tension members wrap the base material around a stretcher, in particular a decontamination stretcher, for transport of the patient.

A clear 20 mil thick PVC material extends upwardly from the base into an over area and terminates at each side at a zipper half. The zipper halves are completely separable so that the apparatus may be opened in a clamshell arrangement and a patient may be laid therein. This is particularly important with patients infected by hemorrhagic fevers such as Ebola or Marburg. Such patients may resist handling. Attempts to place the patient into a prior art isolation system, such as a Vickers box, where there is a relatively small port of entry can be difficult without contaminating the handlers. It may be appreciated that contamination of the environment and other persons must be avoided in order to prevent the spread of these types of virulent viruses.

Accordingly, the present invention, as embodied in the apparatus, is easily closed around the patient without panicking the patient and without unwarranted spread of virus during the process.

The PVC material has a plurality of flexible, nylon ribs or stays positioned in sleeves to provide support. The stays are used to hold the transparent PVC shell away from the patient to allow the patient to be manipulated and to reduce the patient's sense of from being enclosed within the pod. Multiple pairs of glove box ports are provided in the sides of the walls of the unit and at the head end to allow physicians, nurses or other medical professionals to treat the patient within the apparatus without exposing themselves to the infected patient.

A pass-through port is provided for transferring materials in a one way fashion from the outside to the interior of the pod without exposing others. A plurality of small outwardly extending access ports are provided through which may be extended electrocardiographic leads, a suction pump line, infusion lines from a intravenous infusion pump or the like. A larger port is provided for extending a ventilator tube from the outside to a patient to provide ventilation through an airway extending into the patient's trachea. A single glove box port is positioned at the head end of the apparatus to allow a physician or other care giver to intubate the patient.

A plurality of internal storage pouches are provided within the apparatus. The pouches may be preloaded with a variety of supplies such as first aid or medical kits including gauze, tape, various antibiotics, analgesics and the like. The supplies are made available for rapid administration to a patient, particularly a patient who might be in extremis. A pair of patient straps are provided which extend from side to side on the interior of the base to anchor the patient with respect to the base of the pod. While not intended to restrain the patient, they help to maintain the base of the apparatus in contact with the patient so that the upper clear walls of the apparatus are spaced away from the patient and not in contact with him or her.

A blower and filter are provided which may be connected either to the head end or the foot end of the pod. The blower may provide positive pressure to the pod in the event that the patient is uncontaminated and the immediate environment around the patient is contaminated. That is relatively clear air from within the pod would be exhausted to a hot environment. The blower also may be connected to the opposite and of the pod and run in the other direction to provide negative pressure within the pod which is the more usual configuration. This configuration is used when the patient is hot or contaminated and the environment is relatively or completely uncontaminated. This prevents the release of contaminants including pathogens to the environment. Air is drawn in through one of the ports and is exhausted through a filter system at the blower which prevents the pathogens from being released into the environment. The blower, however, when operated in either mode, provides air to the patient so that the patient may breath. The blower may be energized by lithium batteries or D-cell batteries and may have a life for one set of batteries of up to fifteen hours of service time. This is enough time to transport the patient from a casualty site to a hot handling facility.

A drain port is also provided at the foot end of the pod in an end wall thereof. Any liquid which may be present or form within the apparatus due to decontamination or release of contaminated fluids from the patient may be drained out of the apparatus while the patient is isolated inside. Such patient-generated fluids would likely be biologically contaminated. Fluid removal is done simply by elevating the head end of the pod with respect to the foot end and allowing the fluid to travel out by gravity. A patient for instance who might be contaminated with a biological contaminant can be decontaminated within the pod with a rinse such as water or some other liquid decontaminant which may comprise a decontaminant solution.

The blower and filter assembly may be optionally supported by a stand having a sleeve-type clamp. The clamp may be attached to a handle of a decontamination stretcher for convenient support. It allows anchoring the blower and filter assembly substantially fixed with respect to an air inlet at the head end of the apparatus adjacent the head of the patient when the apparatus is to be operated in positive pressure mode. The blower and filter may also be similarly mounted at the front end of the stretcher for operation of the apparatus in the negative pressure mode.

It may also be appreciated that coverings are provided for the port holes for each of the glove box arms so that any glove box arms remaining sealed need not later be decontaminated.

A number of the ports connected to the walls include flexible diaphragms which are opened when connected to the blower and filter assembly and closed when unconnected to maintain isolation between the interior of the apparatus and the surrounding environment.

It is a principal aspect of the invention to provide a portable, inexpensive and easily stored isolation system for isolating a patient from an environment for preventing the transport biological and chemical agents between the environment and the person.

Other aspects and advantages of this invention will become apparent to one of ordinary skill in the art upon a perusal of the following specification and claims in like of the accompanying drawings.

DETAILED DESCRIPTION OF THE PREFERRED EMBODIMENTS

Figure 1:
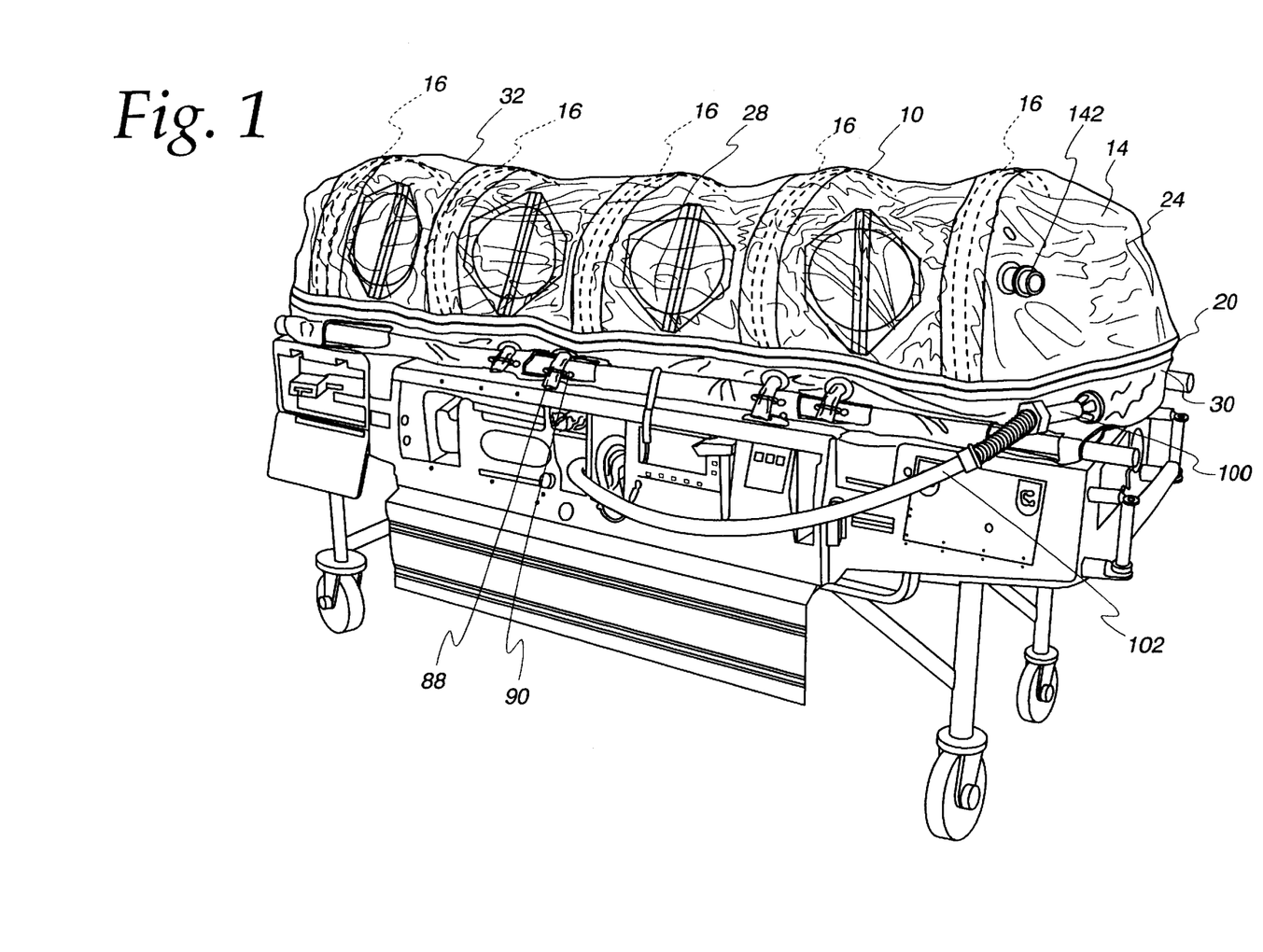
FIG. 1 is a perspective view of an isolation apparatus, specifically an isolation pod, embodying the present invention, having plastic tube stays, having a person lying therein, and being supported by a mobile intensive care rescue facility.
Figure 2:
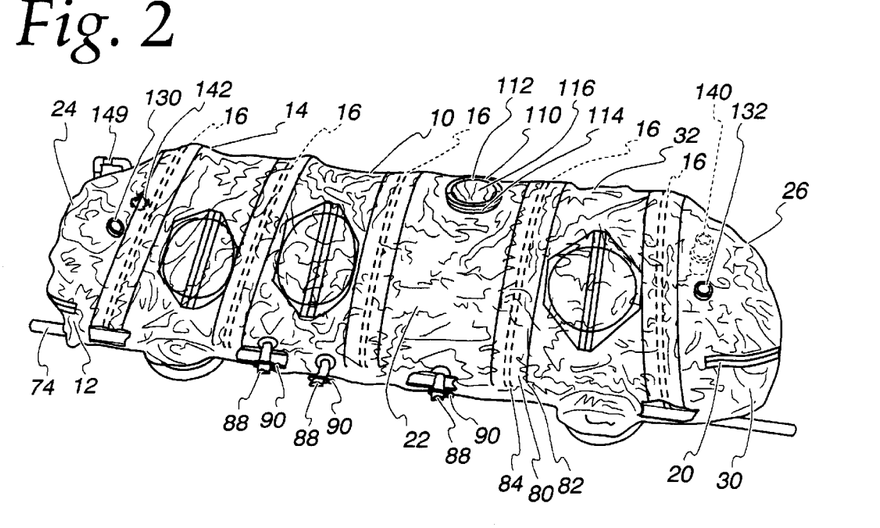
FIG. 2 is a perspective view of the isolation apparatus shown in FIG. 1 but having nylon rod stays and being mounted upon a decontamination stretcher.
Figure 3:
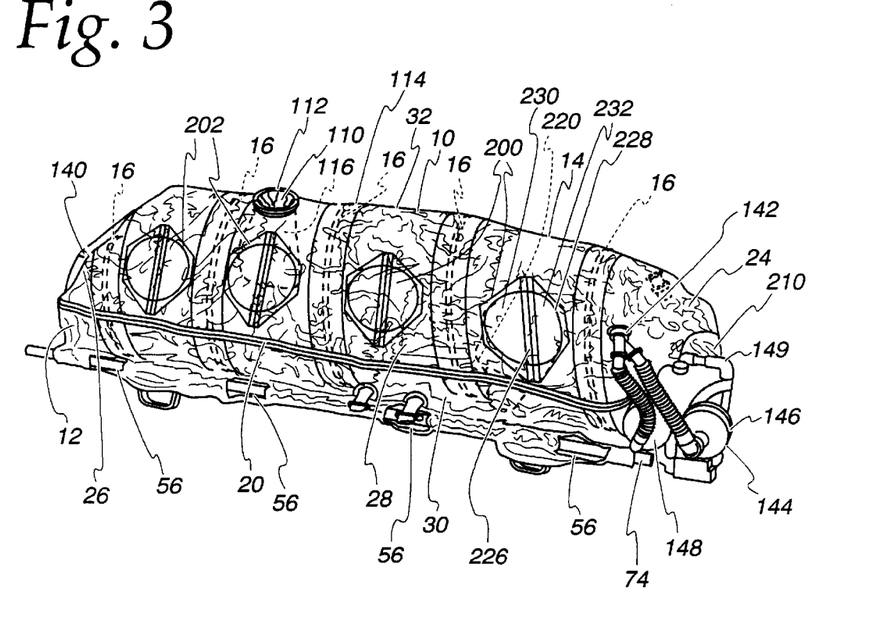
FIG. 3 is a perspective view of the opposite side of the isolation pod shown in FIG. 2 showing details of a zipper closure and a ventilation system.
Figure 4:
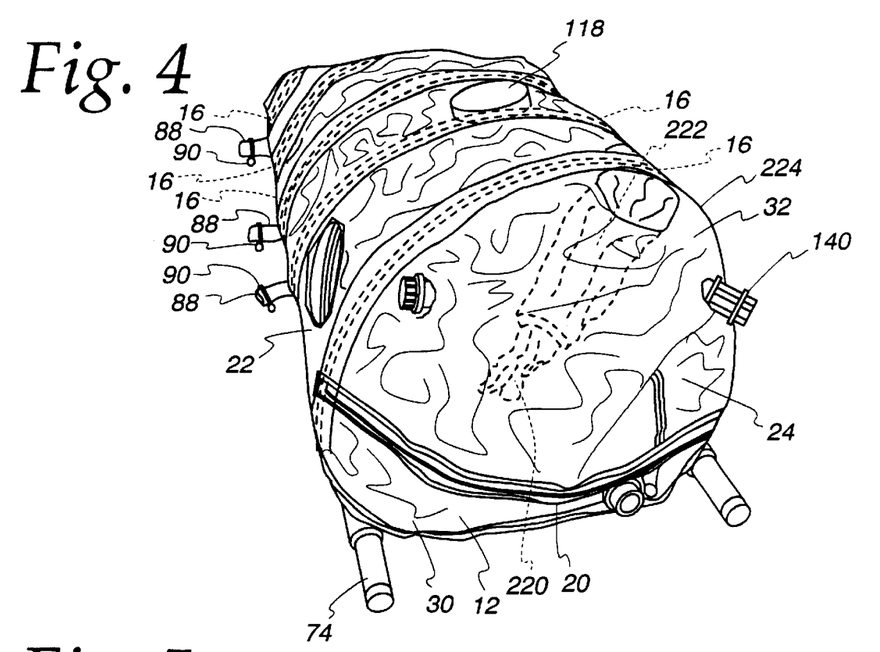
FIG. 4 is an end perspective view of the isolation pod shown in FIG. 2 showing details of the region in which a patient's feet would rest and showing details of a portion of a glove box assembly.
Figure 5:
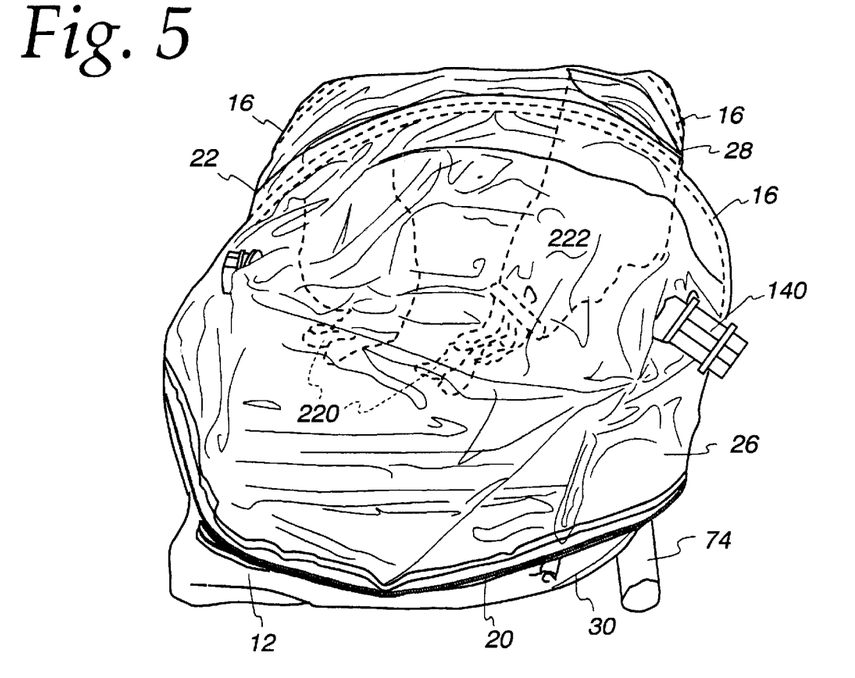
FIG. 5 is a further view of the glove box assembly shown in FIG. 4.

Referring now to the drawings and especially to FIGS. 1 and 2, a collapsible personnel isolation apparatus embodying the present invention is shown therein and generally identified by reference numeral 10. The collapsible isolation apparatus 10 is an isolation pod and includes a flexible base 12 and a transparent cover 14. The transparent cover comprises a transparent flexible polyvinyl chloride wall having a thickness of 20 mils or 0.020 inch. The transparent cover 14 has a plurality of internal supports or stays 16. The stays may be plastic tubes, as shown in FIG. 1 or nylon rods, as shown in FIG. 2. The stays 16 extend through portions of the cover 14 and support it with respect to the base 12 to prevent the cover 14 from collapsing onto a patient who may be placed therein. A closure 20 comprising a zipper extends partially along a back wall 22, completely along a pair of side walls 24 and 26 and a front wall 28. The zipper 20 is a 132–134 inches long gas seal zipper and may be obtained from YKK of Japan. The zipper 20 holds the pod closed and causes the stays to be compressionally curved into arches to support the wall 14. It also provides a clamshell opening configuration defining a bottom 30 and a top 32. The bottom 30 includes the base 12 and a portion of the transparent cover 14. The top 32 includes the remainder of the transparent enclosure 14. The pod 10 is collapsible into a very small volume and may be stored in a duffle bag. It may be rapidly deployed and is self-supporting.

Figure 15:
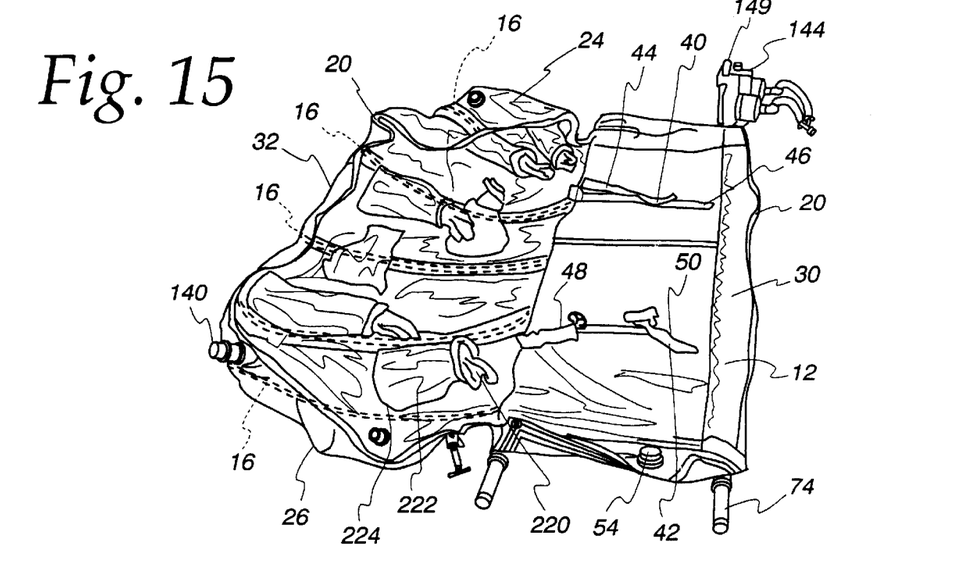
FIG. 15 is a perspective view of the isolation pod shown in FIG. 2 in an open configuration.
Figure 16:
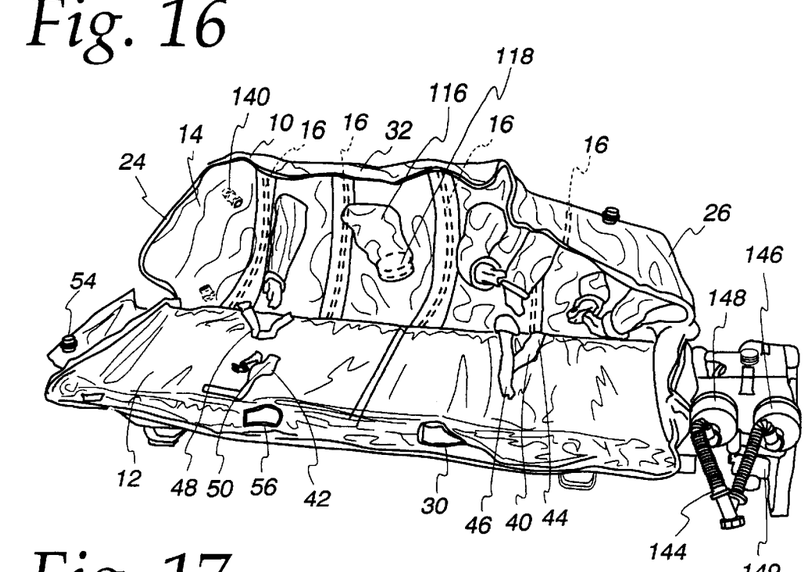
FIG. 16 is another perspective view of the isolation pod shown in FIG. 2 shown in the open configuration.

The clamshell opening configuration allows a patient to be easily placed within the interior of the pod type apparatus providing secure isolation of the patient from the environment and vice-versa. In order to prevent the patient from damaging the pod 10 after having been enclosed therein by enclosing the bottom 30 to the top 32 by way of the zipper a pair of anchoring belts 40 and 42 are provided and are attached to the base. Belt 40 includes a first half 44 and a second half 46. The belt 42 includes a first half 48 and a second half 50, as shown in FIGS. 15 and 16. In addition, the base 12 is provided with a capped drain 54 from which fluids may be drained from the interior of the pod 10 such fluids may be decontamination fluids or fluid materials generated by the patient themself.

The material of the flexible base is constructed of an outer sheet and an inner sheet. Each of the sheets has first and second polyvinyl chloride outer bags with an intermdant nylon mesh layer. A nylon webbing formed in the shape of a ladder includes a pair of uprights or runner elements extending longitudinally on opposite sides of the base 12 for providing support when the base 12 is carried. Lateral or central spaced-type support is provided by five nylon straps connecting the uprights to each other.

Figure 6:
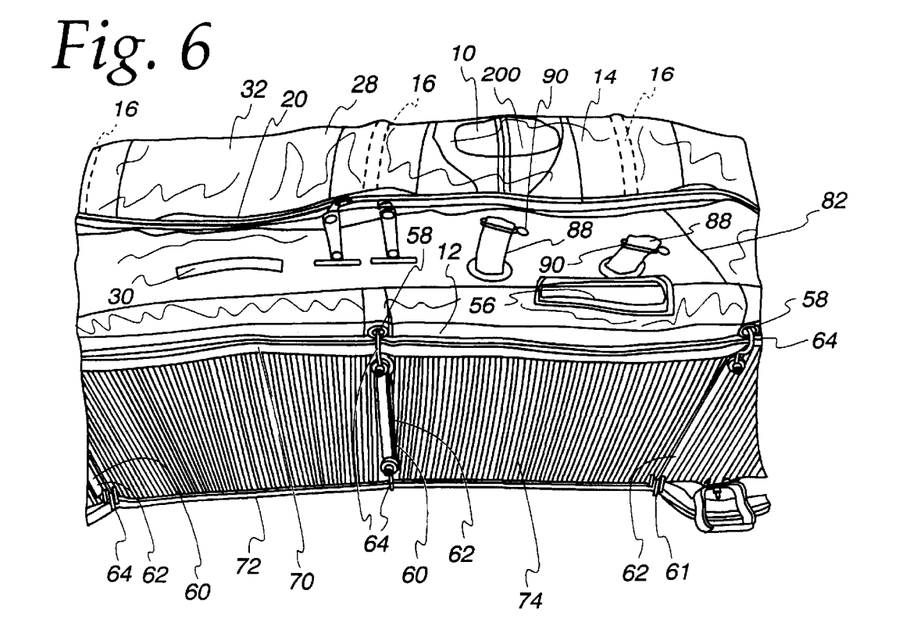
FIG. 6 is a partial perspective view of a portion of the isolation pod shown in FIG. 2 showing details of its attachment to the decontamination stretcher.
Figure 7:
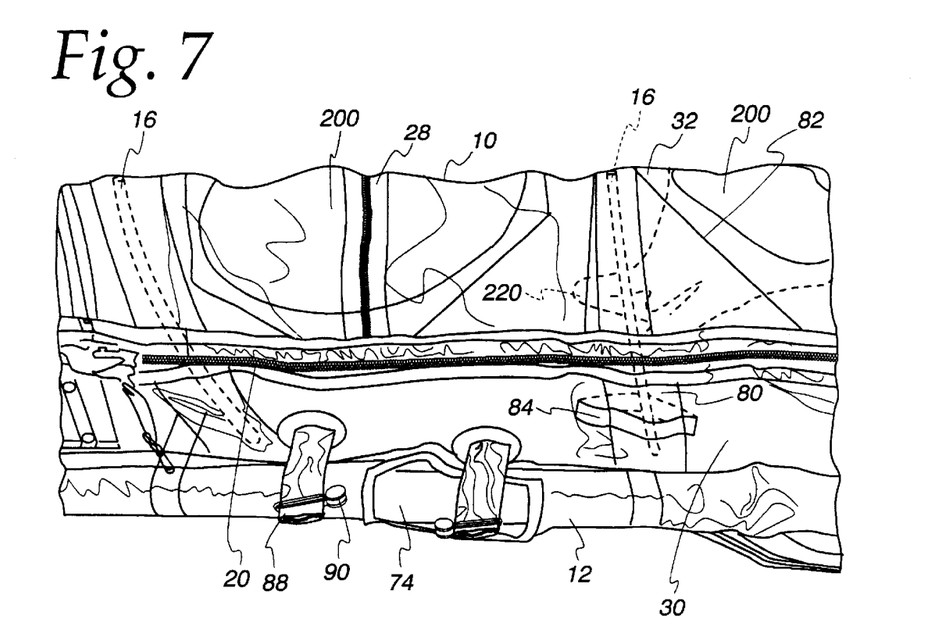
FIG. 7 is a partial perspective view of the isolation pod shown in FIG. 2 showing a pair of clamped-off ports extending from a lower portion thereof and showing details of a handhold.
Figure 8:
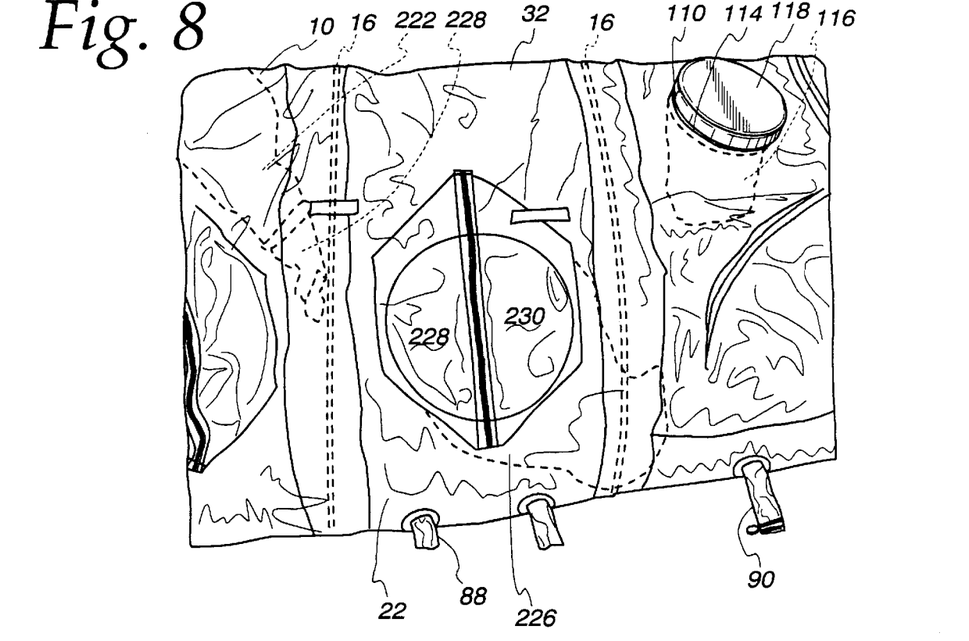
FIG. 8 is a partial perspective view of the isolation pod shown in FIG. 2 and showing a zipper-type sealed opening for a glove arm for manipulation of a patient or instruments within the isolation pod.
Figure 9:
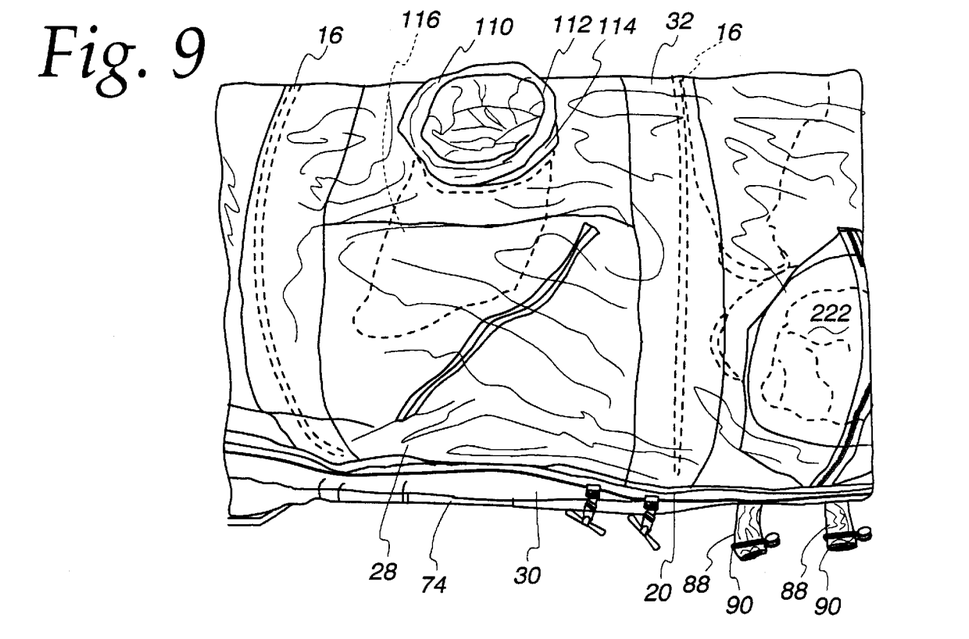
FIG. 9 is a partial perspective view of the isolation pod shown in FIG. 2 showing a transfer port together with a glove port arm.
Figure 10:
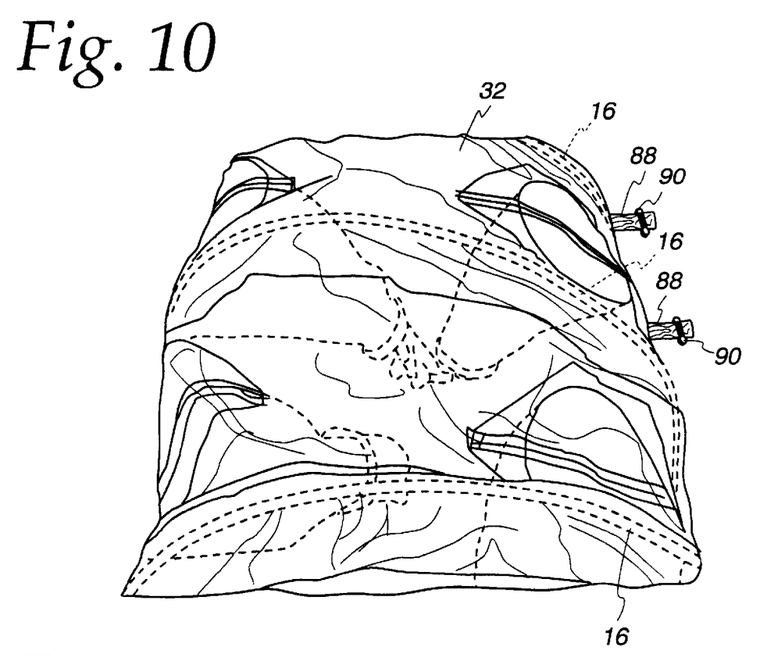
FIG. 10 is a partial perspective view of the isolation pod shown in FIG. 2 showing details of multiple glove pairs therein and multiple access ports.
Figure 11:
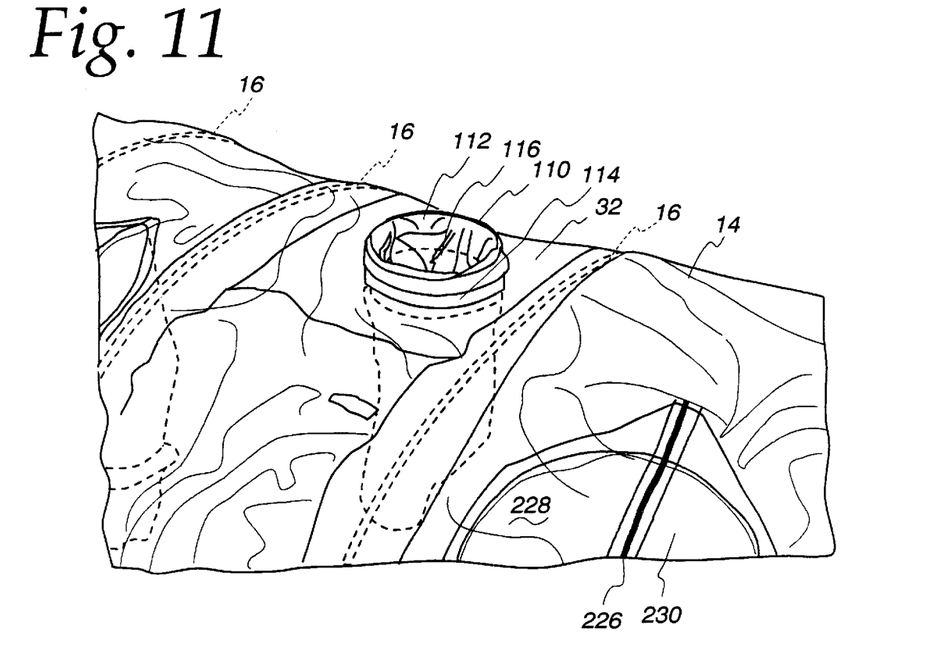
FIG. 11 is partial perspective view of the isolation pod shown in FIG. 2 showing the transfer assembly together with one of the glove box assemblies.
Figure 12:
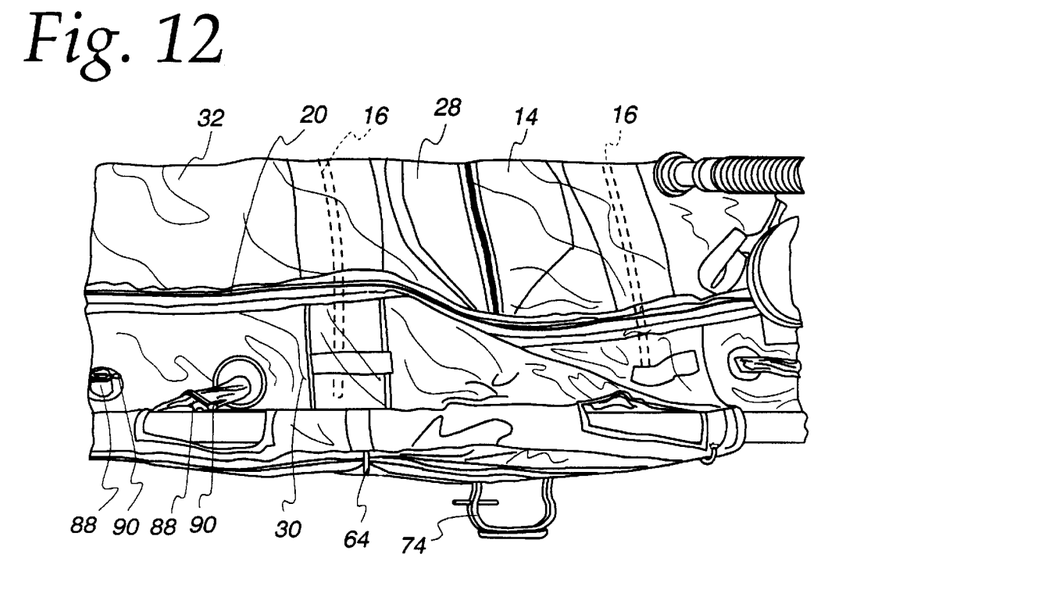
FIG. 12 is a partial side view of the isolation pod shown in FIG. 2 showing the relation between the zippers, the ports and the gloves of the glove box.
Figure 13:
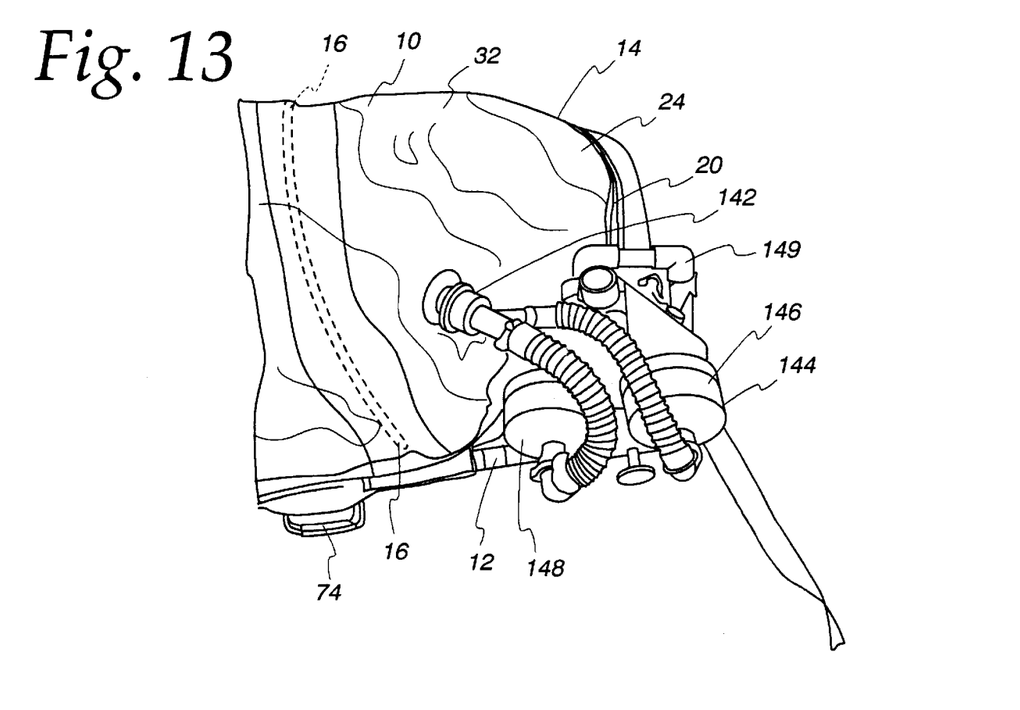
FIG. 13 is a partial perspective view of the isolation pod shown in FIG. 2 showing a ventilation system and its attachment in ventilating communication to an upper portion of the isolation pod.
Figure 14:
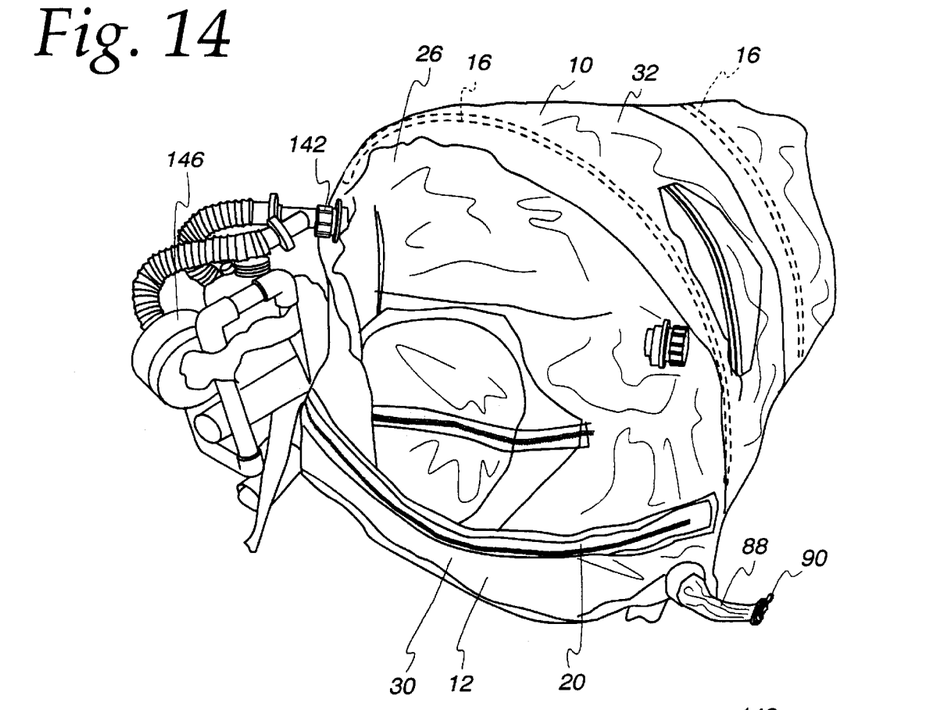
FIG. 14 is an end perspective view of the isolation pod shown in FIG. 2 showing a head end of isolation pod having a single port for use in manually intubating a patient within the isolation pod.

The base 12 has formed therein a plurality of rectangular handholds 56 which may be used to pick up the pod 10 without any supporting structure underneath in order to transport the patient. The base 12 has a plurality of grommets 58 formed therein. The grommets 60 are provided to be connectable with elastic tension members 60 having elastic members 62 and 64 hooks for engaging the grommets 58, as may best be seen in FIG. 6. This allows overlapping base edge portions 70 and 72 to be wrapped around a stretcher 74 to attach the pod 10 securely to the stretcher 74 for transport.

As set forth above, in order to support the upper portion or top 32 of the pod 10 the plurality of internal supports, stays or ribs has been provided. Each of those stays or ribs is confined within a sleeve 80 comprising a strip 82. The strip 82 and top 32 along the outside of the pod 10 define a stay-receiving channel having an entryway formed in the bottom thereof. In alternative embodiments the strips 82 may be attached by heat sealing as opposed to being sown.

In addition the pod 10 includes a plurality of ports including a plurality of small ports for the introduction of EKG apparatus lines, intravenous lines defibrillator lines, suction lines and the like. The ports are positioned in the lower half or bottom of the pod 10 so that the leads may stay connected to the patient whether the pod 10 is open or closed. The small ports 88 are closed with port clips 90 at the ends thereof. In the alternative, when lines are extending through the ports 88 they may be held closed with tape to avoid the communication of contaminants between the inside of the pod and the environment. The ports 88 are typically tapered and may be sown or heat sealed as two halves. The ports 88 are tapered to provide a varying diameter cross-section for receiving a variety of connections thereto.

An enlarged ventilation port 100 is also provided for receiving a ventilator tube 102 for a respirator. The ventilator tube 102 may be connected to an device for forming an airway to the patient's respiratory system.

A pass-through port 110 comprising a double-bagged air lock, is provided with a the top including a large ring 112 with an elastic band 114 surrounding it to engage at least one of a plurality of bags 116 extending into the interior of the opening. The pass-through port 110 may be used to pass plastic bags containing objects through one at a time without breaching the containment of the pod 10. The pass-through port 110 may be optionally covered with a soft plastic top 118 to prevent material from falling inside one of the bags before it is transferred into the interior of the pod 10.

A plurality of drain ports are providing including a drain port 130 and a drain port 132 through which liquids may be drained by gravity by tilting the pod 10 with the patient inside.

In addition, a pair of air stream or general diaphragm or check-valve type ventilator ports 140 and 142 are provided. The ports only provide communication when they are connected to a fitting which opens the internal check valve. One of which is connected to a ventilator 144 having a pair of filters 146 and 148. The ventilator is supported by a PVC tubing support 149 that engages an arm of the stretcher. Ventilation air is carried from the head end port 142 to the tail end port 140. If it is desired to provide positive pressure to the interim of the pod 10 the ventilator 144 is attached to the head end port 142 to provide positive pressure. If it is desired to provide a negative pressure environment in the interior of the pod 10 the ventilator 144 is connected to the port 140 through which it draws air entering the head end port 142. Thus, the interior of the pod 10 may be run either above ambient pressure or below ambient pressure. When run above ambient pressure the pod 10 is configured for use with a contaminated environment and a uncontaminated patient within the pod. When the pod 10 is run below atmospheric pressure air drawn out of the pod is filtered in the filters 148 and 144 before being released to the environment so that a contaminated patient may not spread contamination.

In order to obtain access to the patient sealed in the pod 10 a plurality of glove ports 200 are provided. The glove ports 200 are primarily arranged in pairs with a first pair of glove ports 200 on the front wall, a second pair of glove ports 202 on the front wall, two pairs of glove ports on the back and a single glove port 210 at the head end for access to the patient for incubating the patient when necessary. Each of the glove ports 200 of the glove port pairs includes a glove 220, which may be a substantially unisex latex glove. The glove 220 is connected to a PVC sleeve 222 extending to a glove port opening 224. In addition, the glove port openings 224 have zipper-type closures 226 associated therewith. The closure 226 has a first flap 228 and second flap 230 with a sealing line 232 similar to an overlapping interlock plastic seal formed thereon. The closure 226 prevents material from falling into the open glove arm during transportation or the like. The glove ports 220 may be used to manipulate the patient within the pod 10 without breaking the barrier and releasing contaminants from the pod 10 into the environment or allowing the contaminants from the environment to reach the patient.

Figure 17:
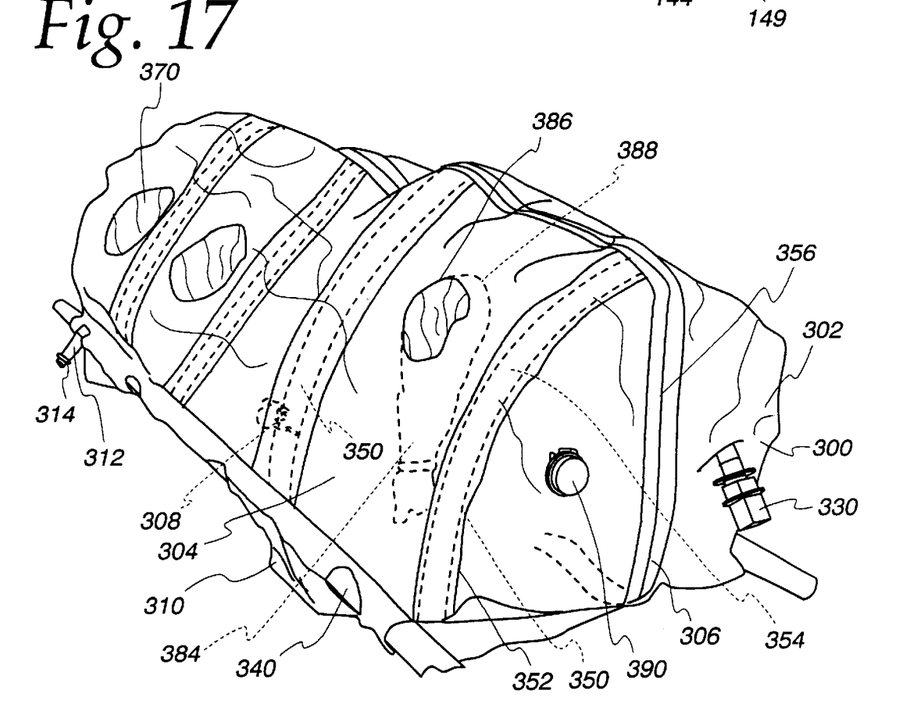
FIGS. 17–19 are perspective views of an alternative embodiment of the isolation pod having a centerline zipper closure.
Figure 18:
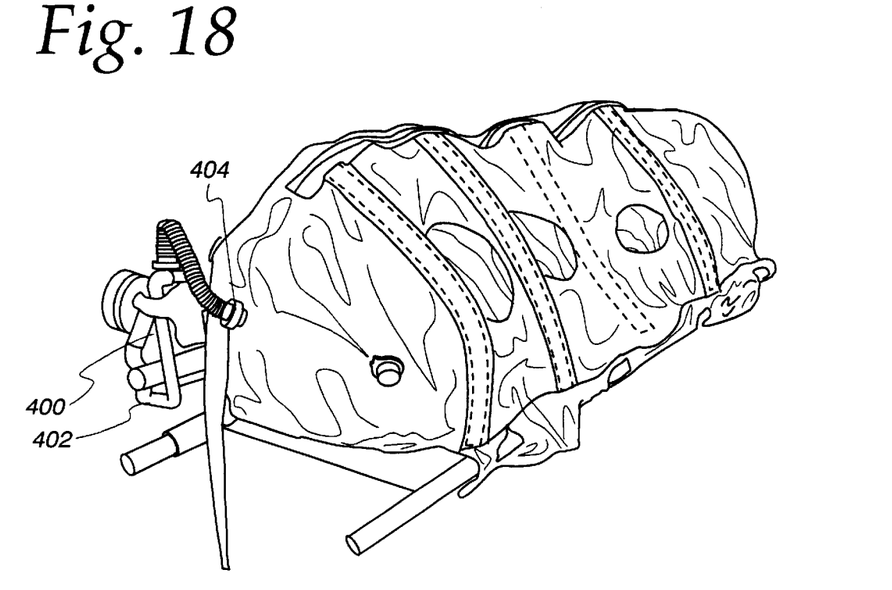
Figure 19:
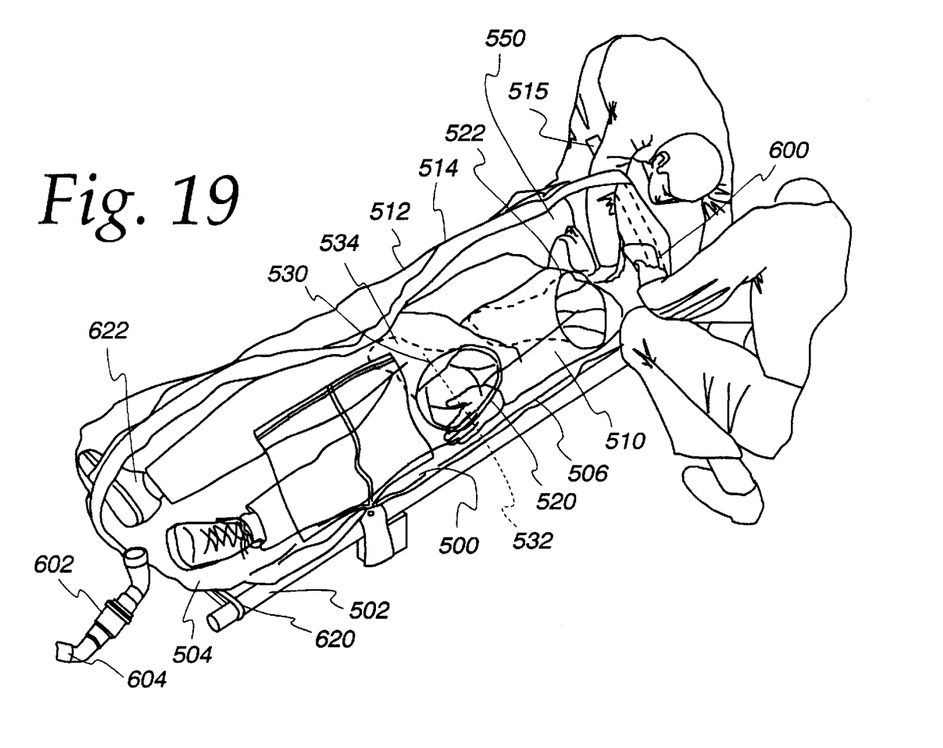

A further embodiment of the present invention is shown in FIGS. 17–19 wherein a pod 300 includes a left transparent PVC pod half 302 and a right transparent PVC pod half 304 joined by a zipper 306 at a center line. The pod 300 includes a plurality of belts 308 for securing the patient to a relatively thick PVC base 310 and includes a plurality of ports 312 having clamps 314 associated therewith for admission of suction lines, defibrillator lines, infusion lines, IV lines, EKG lines and the like. A ventilator port 330 is provided at one end. The pod 300 includes handholds 340 formed in the base thereof. A plurality of stays 350 comprising substantially flat Lexon plastic strips are positioned in sleeves 352 for supporting the pod. The stays are arranged in the stay halves 354 and 356 which provide a tent-like structure.

The pod 300 works in substantially the same fashion as the pod 10. It includes a plurality of glove box ports 370 for the admission of the hands and forearms of a doctor or a nurse treating the patient. The glove box ports 370 terminate in gloves 384 connected to PVC sleeves 386 which are attached to an opening 388. Drain plugs 390 are provided for draining materials from within the pod 300. A ventilator 400, which is substantially identical to the ventilator 142 is positioned on a ventilator support 402 and connected to a check valve port 404 for ventilation of the interior of the pod 300.

A further alternative pod 500 may be positioned on a stretcher 502 and includes a base 504 with an upper portion 506 and a right transparent half 510 and a left transparent half 512 joined by a zipper closure 514. A plurality of glove box ports 520, 522 and 524 are provided for treating the patient. Each of the glove box ports has an opening 530 with a PVC sleeve 532 attached thereto and a latex glove 534. The pod 500 includes a plurality of internal supports or stays 550 comprising flattened ribs which are positioned in sleeves in the walls of the bag to support the bag above the patient. The system includes a head-end glove port 600 and an attachment 602 to which a ventilator 604 may be coupled. The pod may be secured to a stretcher by elastic cords 620 and may accommodate a patient 622 therein.

The present invention may also be incorporated into wraps for civilian use in scenarios involving a limited number of pods for contaminated patients such as might be present in a chemical incident or for persons who would need to have medical attention administered through the wrap. In addition, suits may be provided including a power respirator hood that creates negative pressure within the hood and including rib or other supports for supporting the suit in particular the hood away from the person when the suit is being run in a negative pressure mode to prevent the suit from collapsing around the person.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A collapsible personnel isolation apparatus adapted to be erected in the field from a collapsed compacted form into an expanded form for isolating, transporting and treating a person being transported, the apparatus comprising:

a lower flexible base that is expanded from its collapsed compacted form to allow a person to be laid on the lower flexible base;

an upper flexible cover having a flexible wall to be erected from a collapsed compacted form into an extended cover to be placed over the top of the person laid on the lower flexible base;

a substantially airtight closure device for joining the flexible base and the flexible cover to one another and to provide a substantially airtight interior region for the person therein;

the flexible base and cover defining a pod sized for use with or as a stretcher;

ports in the pod leading from the exterior of the pod into the interior regions to allow access to the patient for treatment from the exterior by a care giver; and a ventilation port for transmission of air between the interior region and the exterior and for providing biochemical isolation between the interior region and the exterior.

2. A collapsible personnel isolation apparatus according to claim 1 wherein said flexible walls are made with flexible plastic material;

the lower flexible base and the upper flexible cover comprising upper and lower clam shell portions joined together by the closure device.

3. A collapsible personnel isolation apparatus according to claim 2 wherein said plastic material comprises a polyvinyl chloride flexible wall having a thickness of about 0.020 inches or less.

4. A collapsible personnel isolation apparatus according to claim 1 wherein the internal support is held in supporting compression with the flexible wall.

5. A collapsible personnel isolation apparatus according to claim 1 further comprising a second ventilation port; one of said ventilation ports being adapted to admit air to the interior, the other of said ventilation ports being adapted to exhaust air from the interior.

6. A collapsible personnel isolation apparatus according to claim 1 wherein the ports comprise a glove port terminating in a glove which is biochemically isolated from the interior but which can be used to manipulate objects within the interior.

7. A collapsible personnel isolation apparatus according to claim 1 wherein the ports comprise a pass-through port formed in a portion of the flexible wall, the pass through port being provided for isolated exchange of items from the exterior to the interior.

8. A collapsible personnel isolation apparatus according to claim 1 further comprising: a filter and blower assembly for chemical and biological environments, the filter and blower assembly being in air transport communication with the ventilation port.

9. A collapsible personnel isolation apparatus according to claim 1 wherein the closure device comprises a zipper.

10. A collapsible personnel isolation apparatus comprising:
 a flexible wall defining an interior region for receiving a patient;
 at least one internal support adapted for supporting contact with the flexible wall to hold it away from the patient;
 a ventilation port for transmission of air between the interior region and exterior of the apparatus and for providing biochemical isolation between the interior region and exterior;
 a zipper enclosure; and
 wherein a plurality of access ports are provided in a lower portion of the flexible wall below the zipper to avoid moving the ports with respect to the patient when the apparatus is opened and closed.

11. A collapsible personnel isolation apparatus comprising:
 a flexible wall defining an interior region for receiving a patient;
 at least one internal support adapted for supporting contact with the flexible wall to hold it away from the patient;
 a ventilation port for transmission of air between the interior region and exterior of the apparatus and for providing biochemical isolation between the interior region and exterior; and
 a flexible base connected to the flexible wall to define the interior, the flexible base being thicker than the flexible wall.

12. A collapsible personnel isolation apparatus according to claim 11 wherein the flexible base comprises a plurality of handholds formed therein for carrying the personnel isolation apparatus when it is loaded with a patient.

13. A collapsible personnel isolation apparatus according to claim 12 wherein the flexible base further comprises apparatus formed in the flexible base for engagement by elastic tension members for strapping the flexible base about a stretcher to provide support when carrying a patient within the interior.

14. An erectable isolation pod for transporting and treating persons, the pod comprising:
 a collapsible lower base portion positioned to be laid on the ground and uncovered to allow a person to lie down on the base;
 a collapsible upper cover portion to be positioned over the patient laying on the base and to be joined to the base portion to enclose the patient;
 a substantially airtight closure device joining the lower base portion and the upper cover portion to enclose the patient in a substantial airtight interior region;
 a portable air filtration unit connected to an air port in the joined base portion and cover portion for the transmission of air between the interior region and exterior of the pod while the portable air filtration unit and the patient are being transported to a hospital;
 ports in pod to allow treatment of the patient in the interior region of the pod by care givers on the exterior of the pod;
 the closure device extending along substantially at least one side of the pod and along substantially at least one short end of the pod.

15. An isolation pod in accordance with claim 14 wherein the closure device comprises a zipper and joins together at least one long side and a head end and a foot end of the base portion and cover portion to enclose the patient in the pod.

16. An isolation pod in accordance with claim 14 comprising:
 at least one internal support within the pod to hold the cover portion away from the patient; and
 an air blower for blowing air into the pod to provide the patient with air and to provide compressed air in the interior region to hold the cover portion from the patient.

17. An isolation pod in accordance with claim 14 comprising:
 a stretcher-like pod sized to be used as a stretcher or with stretcher poles.

18. A stretcher kind of collapsible isolation apparatus for use in transporting and treating a patient in an isolated interior chamber in the apparatus, the apparatus comprising:
 a bottom portion to receive a patient laid on his back on an interior side of the bottom portion;
 the bottom portion sized to be used as or with a stretcher to transport the patient;
 a cover portion for joining to the bottom portion to define the isolated interior chamber in the apparatus and about the patient;
 the bottom and cover portions defining a collapsible apparatus that may be expanded to receive a patient;
 ports in the cover portion to allow treatment of the patient within the interior chamber by a care giver on the exterior of the cover portion while the patient is being transported;
 a portable air ventilation and filtration device mounted on one end of the base to be transportable on the stretcher with the base;
 an air filter on the ventilation and filtration device for connection to ports for the chamber in a first mode to filter air flowing into the hollow interior chamber and for connection in a second mode to filter air flowing from the interior chamber.

19. A stretcher kind of apparatus in accordance with claim 18 comprising:
 patient restraining belts mounted within the bottom portion to restrain the patient while being transported on a stretcher.

20. A stretcher kind of apparatus in accordance with claim 19 comprising:
 connectors on the base portion for connection thereof to a stretcher.

21. A stretcher kind of apparatus in accordance with claim 18 wherein:
 the air ventilation and filtration device comprises a pair of filters;
 a common hose connected to the pair of filters and being in fluid communication with a first port for the chamber when filtering air flowing into the chamber and being in fluid communication with a second port for the chamber when filtering air flowing from the chamber.

* * * * *